US012268804B2

(12) United States Patent
Niimi et al.

(10) Patent No.: US 12,268,804 B2
(45) Date of Patent: *Apr. 8, 2025

(54) BLOOD CIRCULATION SYSTEM

(71) Applicant: SENKO MEDICAL INSTRUMENT MFG. CO., LTD., Tokyo (JP)

(72) Inventors: Yoshinari Niimi, Tokyo (JP); Masahiro Kamiya, Tokyo (JP)

(73) Assignee: SENKO MEDICAL INSTRUMENT MFG. CO., LTD., Tokyo (JP)

( * ) Notice: Subject to any disclaimer, the term of this patent is extended or adjusted under 35 U.S.C. 154(b) by 834 days.

This patent is subject to a terminal disclaimer.

(21) Appl. No.: 17/498,422

(22) Filed: Oct. 11, 2021

(65) Prior Publication Data

US 2022/0023523 A1 Jan. 27, 2022

Related U.S. Application Data

(63) Continuation of application No. 16/006,277, filed on Jun. 12, 2018, now Pat. No. 11,141,519, which is a
(Continued)

(30) Foreign Application Priority Data

Aug. 20, 2014 (JP) .................................. 2014-167559
Mar. 17, 2015 (JP) .................................. 2015-053600

(51) Int. Cl.
*A61M 1/36* (2006.01)
*A61M 1/16* (2006.01)
(Continued)

(52) U.S. Cl.
CPC ........ *A61M 1/3666* (2013.01); *A61M 1/1603* (2014.02); *A61M 1/1629* (2014.02);
(Continued)

(58) Field of Classification Search
CPC .... A61M 1/14; A61M 1/1006; A61M 1/1086; A61M 1/3666; A61M 1/3639;
(Continued)

(56) References Cited

U.S. PATENT DOCUMENTS 4,598,697 A * 7/1986 Numazawa ........... A61M 60/38
604/6.11
4,650,457 A 3/1987 Morioka et al.
(Continued)

FOREIGN PATENT DOCUMENTS

CN 102365105 2/2012
DE 3720667 A1 1/1989
(Continued)

OTHER PUBLICATIONS

International Search Report and Written Opinion for PCT App No. PCT/JP2015/073428 dated Nov. 2, 2015, 8 pgs.
(Continued)

*Primary Examiner* — Leslie R Deak
(74) *Attorney, Agent, or Firm* — PROCOPIO, CORY, HARGREAVES & SAVITCH LLP

(57) ABSTRACT

A blood circulation system that can be connected to a human body is provided. The system may include a roller pump, a blood removal line through which blood removed from the human body flows to the roller pump, a blood transfer line that transfers blood, which is sent from the roller pump, to the human body, means for measuring a blood removal rate provided in the blood removal line to measure a blood removal rate parameter of blood flowing through the blood removal line and a control unit, wherein the control unit is programmed to control a blood transfer rate of the roller pump by controlling a rotational speed of the roller pump with a control signal, such that a transfer rate of blood flowing through the blood transfer line is synchronized with
(Continued)

a removal rate calculated from the blood removal rate parameter.

4 Claims, 9 Drawing Sheets

Related U.S. Application Data continuation of application No. 15/502,949, filed as application No. PCT/JP2015/073428 on Aug. 20, 2015, now Pat. No. 11,040,132.

(51) Int. Cl.
| | |
|---|---|
| *A61M 60/104* | (2021.01) |
| *A61M 60/113* | (2021.01) |
| *A61M 60/232* | (2021.01) |
| *A61M 60/279* | (2021.01) |
| *A61M 60/38* | (2021.01) |
| *A61M 60/411* | (2021.01) |
| *A61M 60/427* | (2021.01) |
| *A61M 60/523* | (2021.01) |
| *A61M 60/546* | (2021.01) |

(52) U.S. Cl.
CPC ........ *A61M 1/1698* (2013.01); *A61M 1/3623* (2022.05); *A61M 1/3624* (2013.01); *A61M 1/3639* (2013.01); *A61M 60/104* (2021.01); *A61M 60/113* (2021.01); *A61M 60/232* (2021.01); *A61M 60/279* (2021.01); *A61M 60/38* (2021.01); *A61M 60/411* (2021.01); *A61M 60/427* (2021.01); *A61M 60/523* (2021.01); *A61M 60/546* (2021.01); *A61M 2205/18* (2013.01); *A61M 2205/3303* (2013.01); *A61M 2205/3306* (2013.01); *A61M 2205/3334* (2013.01); *A61M 2205/3365* (2013.01); *A61M 2205/3375* (2013.01); *A61M 2205/50* (2013.01); *A61M 2205/502* (2013.01)

(58) Field of Classification Search
CPC ........ A61M 1/1629; A61M 2205/3365; A61M 1/101; A61M 60/523; A61M 60/113
See application file for complete search history.

(56) References Cited

U.S. PATENT DOCUMENTS

| | | | |
|---|---|---|---|
| 5,813,972 | A | 9/1998 | Nazarian et al. |
| 6,024,692 | A * | 2/2000 | Dilling ................ A61M 1/3621 600/16 |
| 11,141,519 | B2 * | 10/2021 | Niimi ................ A61M 1/3624 |
| 2007/0158247 | A1 | 7/2007 | Carr et al. |
| 2010/0042259 | A1 | 2/2010 | Simons |
| 2010/0106101 | A1 | 4/2010 | Fisher et al. |
| 2012/0273415 | A1 * | 11/2012 | Gerber ................ A61M 1/361 210/741 |
| 2012/0330214 | A1 | 12/2012 | Peters et al. |
| 2014/0216250 | A1 * | 8/2014 | Meyer ................ A61M 1/152 95/1 |
| 2015/0045712 | A1 | 2/2015 | Ninomiya et al. |

FOREIGN PATENT DOCUMENTS

| | | |
|---|---|---|
| DE | 19622184 A1 | 12/1997 |
| EP | 0659444 A1 | 6/1995 |
| EP | 2044965 A2 | 4/2009 |
| EP | 2519282 B1 | 11/2012 |
| EP | 2711037 | 3/2014 |
| GB | 2538577 | 11/2016 |
| JP | S62-027966 | 2/1987 |
| JP | S63-143078 | 6/1988 |
| JP | 2000-000299 | 1/2000 |
| JP | 2000210381 A | 8/2000 |
| JP | 2000245829 A | 9/2000 |
| JP | 2001-517495 A | 10/2001 |
| JP | 2006-020712 | 1/2006 |
| JP | 2006043045 A | 2/2006 |
| JP | 2006325750 | 12/2006 |
| JP | 2010-517734 A | 5/2010 |
| JP | 2011147710 A | 8/2011 |
| JP | 2013501578 A | 1/2013 |
| JP | 2014046026 A | 3/2014 |
| WO | 80/02376 A1 | 11/1980 |
| WO | 92/02264 A1 | 2/1992 |
| WO | 99/15212 A1 | 4/1999 |
| WO | 2011019655 A2 | 2/2011 |
| WO | 2011/079941 A1 | 7/2011 |
| WO | 2012141756 | 10/2012 |
| WO | 2013/012776 A1 | 1/2013 |
| WO | 2013025826 | 2/2013 |
| WO | 2013/128016 A1 | 9/2013 |
| WO | 2013128012 A1 | 9/2013 |
| WO | 2014/121164 A1 | 8/2014 |
| WO | 2015041150 | 3/2015 |

OTHER PUBLICATIONS

International Search Report and Written Opinion for PCT App No. PCT/JP2015/073425 dated Nov. 2, 2015, 9 pgs.
International Search Report and Written Opinion for PCT App No. PCT/JP2015/073363 dated Nov. 2, 2015, 9 pgs.
Communication Pursuant to Artilcel 94(3) EPC for EP App No. 15833783.2 dated Apr. 20, 2018, 5 pgs.
Chinese Office Action for CN App No. 201580042928.9 dated Dec. 18, 2017, 12 pgs.
Extended European Search Report for EP App No. 15832993.8 dated Jun. 23, 2017, 7 pgs.
Extended European Search Report for EP App No. 15833783.2 dated Jun. 29, 2017, 8 pgs.
International Preliminary Report on Patentability for PCT App No. PCT/JP2015/073428 dated Nov. 2, 2015, 7 pgs.
Office Action for JP Patent Application No. 2015-114878, mailed on Jan. 8, 2019, in 6 pages.
Notice of Reasons for Rejection for related JP App No. 2015-146146 dated Feb. 5, 2019, 6 pgs.
Office Action for related U.S. Appl. No. 15/502,091 dated Apr. 16, 2019, 38 pages.
Notice of Reasons for Rejection for related JP App No. 2015-157773 dated Jul. 23, 2019, 6 pgs.
Office Action for related U.S. Appl. No. 15/502,949 dated Sep. 19, 2019, 7 pages.
Office Action for related EP App. No. 15833016.7 dated Sep. 19, 2019, 25 pages.
Machine translation of EP 0 659 444 A1 to Hahn (Year: 1993).
EPO; Office Action issued in European Patent Application No. 15833016.7, mailed Apr. 14, 2022, 145 pages.

* cited by examiner

BLOOD CIRCULATION SYSTEM

CROSS-REFERENCE TO RELATED APPLICATIONS

This application is a continuation of U.S. application Ser. No. 16/006,277, filed Jun. 12, 2018, which is a continuation of U.S. application Ser. No. 15/502,949, filed Feb. 9, 2017, which is a US National Stage of International Application PCT/JP2015/073428, filed Aug. 20, 2015, which claims the benefit of foreign priority from Japanese Application No. JP2015-053600, filed Mar. 17, 2015 and Japanese Application No. JP2014-167559, filed August 2014, the contents of each of which are incorporated by reference herein.

TECHNICAL FIELD

The present invention relates to a blood circulation system that circulates removed blood via a blood transfer pump. This application is a Continuation of U.S. patent application Ser. No. 16/006,277, filed Jun. 12, 2018, which is a Continuation of U.S. patent application Ser. No. 15/502,949, filed Feb. 9, 2017, which is a U.S. National Stage entry of PCT Application No. PCT/JP2015/073428, filed Aug. 20, 2015, which claims priority to Japanese Patent Application No. 2014-167559, filed Aug. 20, 2014, and Japanese Patent Application No. 2015-53600, filed Mar. 17, 2015, the contents of which are incorporated herein by reference.

BACKGROUND ART

In the related art, an artificial heart and lung and a blood circulation system for adjunctively circulating blood are widely used as necessary when a heart is stopped or is approximately stopped during or after a surgery such as cardiac surgery.

As shown in FIG. 9, an artificial heart and lung apparatus (blood circulation system) 500 equipped with an artificial heart and lung in the related art includes a blood removal line 501; a reservoir 502; a blood line 503; a blood transfer line 504; a first blood transfer line 505; an artificial lung 506; and a second blood transfer line 507.

The blood removal line 501 transfers blood, which has been received from a vein of a patient (human body) P, to the reservoir 502. The blood removal line 501 is a tube formed of resin such as polyvinyl chloride.

The reservoir 502 includes a tank therein, and temporarily stores the transferred blood.

The blood transfer pump 504 transfers the blood stored in the reservoir 502 to the artificial lung 506 via the blood line 503 through which the reservoir 502 is connected to the blood transfer pump 504, and via the first blood transfer line 505 through which the blood transfer pump 504 is connected to the artificial lung 506. For example, a roller pump or a centrifugal pump is used as the blood transfer pump 504. The blood transfer pump 504 is controlled by a signal output from a blood transfer pump control unit 540.

The artificial lung 506 includes a hollow fiber membrane, a flat membrane, or the like having good gas permeability, and has the function of discharging carbon dioxide from and adding oxygen to blood.

The second blood transfer line 507 receives the blood, from which carbon dioxide has been discharged and to which oxygen has been added by the artificial lung 506, and transfers the blood to an artery of the patient P.

Advanced knowledge and techniques are required to operate the artificial heart and lung apparatus 500 with such a configuration. Typically, a clinical engineer adjusts a blood flow rate via a manual operation according to a doctor's instructions.

When adjusting the blood flow rate via a manual operation, the clinical engineer is required to adjust a blood flow rate in the blood removal line 501 by pinching the blood removal line 501 with a forceps while confirming the degree of removal of blood or an arterial pressure of the patient.

Since the clinical engineer adjusts the amount of discharge of the blood transfer pump by manually controlling the rotational speed of the blood transfer pump (roller pump or centrifugal pump) when adjusting the blood flow rate, a complex and advanced operation technique is required in addition to the adjustment of each line.

Patent Document 1 discloses technology to adjust a blood removal rate in which the blood removal line 501 is pinched and deformed to accurately and simply adjust the blood removal rate via an artificial heart and lung apparatus.

In order to adjust the flow rate of blood to be removed via the blood removal line 501, the artificial heart and lung apparatus disclosed in Patent Document 1 pinches and deforms the blood removal line 501 by operating a blood removal regulator 521, which includes a clamper formed of a pair of clamp members and a servo motor, via a blood removal regulator operation unit 520.

Patent Document 2 discloses technology in which a blood removal regulator control unit is interlocked with a blood transfer regulator control unit, a blood removal rate and a blood transfer rate are simultaneously controlled via operation of one of the control units, and thus a blood flow rate of an artificial heart and lung apparatus is efficiently adjusted.

CITATION LIST

Patent Document

[Patent Document 1] Japanese Unexamined Patent Application, First Publication No. 62-027966

[Patent Document 2] Japanese Unexamined Patent Application, First Publication No. 2006-020712

SUMMARY OF INVENTION

Technical Problem

The amount of blood to be removed may change depending on surgical situations, and it may be difficult to promptly and stably transfer an amount of blood corresponding to a blood removal rate in a case where the blood removal rate changes significantly.

A blood circulation system which circulates removed blood via a blood transfer pump requires technology by which blood is stably circulated at a suitable flow rate.

The present invention is made in light of this problem, and an object of the present invention is to provide a blood circulation system that is capable of stably circulating removed blood at a suitable flow rate via a blood transfer pump.

Solution to Problem

In order to solve this problem, the present invention proposes the following means.

According to a first aspect of the present invention, there is provided a blood circulation system that can be connected to a human body, and transfers removed blood to the human body via a blood transfer pump, the system including: the blood transfer pump; a blood removal line through which removed blood flows to the blood transfer pump; a blood transfer line that transfers blood, which is sent from the blood transfer pump, to the human body; blood removal rate measurement means that is provided in the blood removal line; and a control unit, in which, according to a blood removal rate parameter measured by the blood removal rate measurement means, the control unit controls a blood transfer rate of the blood transfer pump such that the transfer rate of blood flowing through the blood transfer line is in a specific range with respect to the removal rate of blood flowing through the blood removal line.

In the blood circulation system of the invention, according to the blood removal rate parameter measured by the blood removal rate measurement means, the control unit controls the blood transfer rate of the blood transfer pump such that the transfer rate of blood flowing through the blood transfer line is in a specific range with respect to the removal rate of blood flowing through the blood removal line. Therefore, it is possible to ensure that the blood transfer rate is in the specific range with respect to the blood removal rate.

As a result, even if the blood removal rate changes, it is possible to transfer an amount of blood to the human body at a blood removal rate in a specific range, and it is possible to stably circulate blood at a suitable flow rate.

In the present invention, the blood removal line represents a blood line among blood lines of the blood circulation system which is formed such that blood removed from the human body flows through the blood line toward the blood transfer pump. More specifically, the blood removal line represents a blood line leading toward a reservoir. The blood transfer line represents a blood line leading toward the human body from the blood transfer pump.

In a blood circulation path, a blood line, which is positioned on the downstream side of a portion (for example, reservoir) in which blood opens to a space and in which there is no normal continuity of a blood flow rate, may not represent the blood removal line or the blood transfer line.

For the sake of convenience, a blood line may indicate a portion of the blood removal line and the blood transfer line.

In the present invention, the specific range with respect to the blood removal rate implies that the blood transfer rate is in a range which is set with respect to the blood removal rate. The amount of deviation of the blood transfer rate with respect to the blood removal rate is represented by a difference in flow rate (for example, an upper limit or lower limit difference in flow rate) with respect to the blood removal rate.

In the present invention, needless to say, the blood removal rate measurement means includes measurement means for measuring a blood removal rate, and includes measurement means for measuring various blood removal rate parameters for specifying a blood removal rate.

Needless to say, the blood removal rate parameters include a blood removal rate, and are parameters which change corresponding to a blood removal rate. That is, the blood removal rate parameters include various parameters for specifying a blood removal rate, for example, the flow speed of removed blood in a case where a cross-sectional flow path area of the blood removal line is already known, and a parameter (for example, a change in ultrasonic wave frequency) for specifying the flow speed.

In the present invention, in a case where according to the blood removal rate parameter, control is performed such that the blood transfer rate is in a specific range with respect to the blood removal rate, the blood removal rate may not be calculated and the blood transfer pump may be directly controlled according to a measured value of the blood removal rate parameter.

According to a second aspect of the present invention, in the first aspect, according to the blood removal rate parameter measured by the blood removal rate measurement means, the control unit controls the blood transfer rate of the blood transfer pump such that the transfer rate of blood flowing through the blood transfer line is synchronized with the removal rate of blood flowing through the blood removal line.

In the blood circulation system of the invention, according to the blood removal rate parameter measured by the blood removal rate measurement means, the control unit controls the blood transfer rate of the blood transfer pump such that the transfer rate of blood flowing through the blood transfer line is synchronized with the removal rate of blood flowing through the blood removal line. Therefore, it is possible to transfer the same amount of blood as the amount of removed blood to the human body.

As a result, even if the blood removal rate changes, it is possible to transfer the same amount of blood as the amount of removed blood to the human body, and it is possible to stably circulate blood at a suitable flow rate.

In the present invention, the synchronization of the transfer rate of blood flowing through the blood transfer line with the removal rate of blood flowing through the blood removal line implies that the blood transfer rate of the blood transfer pump is controlled to be the same as the blood removal rate. That is, errors caused by a time lag of a control signal output to the blood transfer pump or a response time of the blood transfer pump are allowed.

The synchronization includes not only a case in which the blood removal rate exactly coincides with the blood transfer rate, but also a case in which the blood removal rate substantially coincides with the blood transfer rate.

The synchronization includes a case in which the same amount of blood as the amount of removed blood is transferred by the blood transfer pump while the transferring of blood is delayed by an amount of time set in advance.

According to a third aspect of the present invention, the first and second aspects further include a correction process setting unit, in which, according to correction process data input to the correction process setting unit, the control unit performs correction such that the blood transfer rate of the blood transfer pump corresponds to the blood removal rate.

In the blood circulation system of the invention, the correction process setting unit is provided, and according to the correction process data input to the correction process setting unit, the control unit performs correction such that the blood transfer rate of the blood transfer pump corresponds to the blood removal rate. In a case where a combination of the blood removal rate measurement means and the blood transfer pump is changed, and the blood transfer rate of the blood transfer pump controlled by the blood removal rate parameter does not correspond to the blood removal rate due to individual variations of the blood removal rate measurement means and the blood transfer pump, the blood transfer rate can be efficiently corrected to correspond to the blood removal rate.

According to a fourth aspect of the present invention, the first to third aspects further include a roller pump that is the blood transfer pump, in which the control unit controls the rotational speed of the roller pump according to the blood removal rate parameter measured by the blood removal rate measurement means.

In the blood circulation system of the invention, the roller pump is included as the blood transfer pump, and the control unit controls the rotational speed of the roller pump according to the blood removal rate parameter measured by the blood removal rate measurement means. As a result, the blood circulation system is prevented from being affected by pressure, and it is possible to ensure a stable blood transfer rate by controlling the rotational speed.

According to a fifth aspect of the present invention, the first to third aspects further include blood transfer rate measurement means that is provided in the blood transfer line, in which the control unit controls the blood transfer pump by comparison of a blood transfer rate parameter measured by the blood transfer rate measurement means with the blood removal rate parameter measured by the blood removal rate measurement means.

In the blood circulation system of the invention, the blood transfer rate measurement means is provided in the blood transfer line, and the control unit controls the blood transfer pump by comparison of the blood transfer rate parameter measured by the blood transfer rate measurement means with the blood removal rate parameter measured by the blood removal rate measurement means. Therefore, it is possible to efficiently reduce the difference between the blood transfer rate and the blood removal rate.

As a result, it is possible to efficiently make the blood transfer rate correspond to the blood removal rate, and it is possible to perform stable blood circulation.

In the present invention, needless to say, the blood transfer rate measurement means includes measurement means for measuring a blood transfer rate, and includes measurement means for measuring various blood transfer rate parameters for specifying a blood transfer rate.

Needless to say, the blood transfer rate parameters include a blood transfer rate, and are parameters which change corresponding to a blood transfer rate. That is, the blood transfer rate parameters include various parameters for specifying a blood removal rate, for example, the flow speed of transferred blood in a case where a cross-sectional flow path area of the blood transfer line is already known, and a parameter (for example, a change in ultrasonic wave frequency) for specifying the flow speed.

A comparison between a blood transfer rate parameter and a blood removal rate parameter implies any one of a comparison therebetween in a case where the types of the blood transfer rate parameter and the blood removal rate parameter are the same, a direct comparison therebetween in a case where the types of the blood transfer rate parameter and the blood removal rate parameter are different from each other, and a comparison therebetween after one or both of the blood transfer rate parameter and the blood removal rate parameter are converted into forms in which both can be compared to each other.

According to a sixth aspect of the present invention, the fifth aspect further includes a centrifugal pump that is the blood transfer pump, in which the control unit controls the rotational speed of the centrifugal pump.

In the blood circulation system of the invention, the centrifugal pump is included as the blood transfer pump, and the control unit controls the rotational speed of the centrifugal pump by comparison of the blood transfer rate parameter measured by the blood transfer rate measurement means with the blood removal rate parameter measured by the blood removal rate measurement means. As a result, it is possible to promptly and stably transfer blood, the transfer rate of which corresponds to a blood removal rate.

According to a seventh aspect of the present invention, in the first to sixth aspects, flow rate adjustment means is provided in the blood removal line.

In the blood circulation system of the invention, the flow rate adjustment means is provided in the blood removal line, and thus, it is possible to efficiently adjust the blood removal rate.

According to an eighth aspect of the present invention, in the first to third, fifth and sixth aspects, flow rate adjustment means is provided in both the blood removal line and the blood transfer line.

In the blood circulation system of the invention, the flow rate adjustment means is provided in both the blood removal line and the blood transfer line, and thus, it is possible to efficiently adjust a blood flow rate. If the blood transfer pump is a centrifugal pump, it is possible to prevent the back flowing of blood when the centrifugal pump stops.

Advantageous Effects of Invention

The blood circulation system of the invention is capable of transferring blood such that the blood transfer rate of the blood transfer pump corresponds to the blood removal rate.

As a result, even if the blood removal rate changes, it is possible to stably circulate blood at a suitable flow rate.

DESCRIPTION OF EMBODIMENTS

First Embodiment

Figure 2:
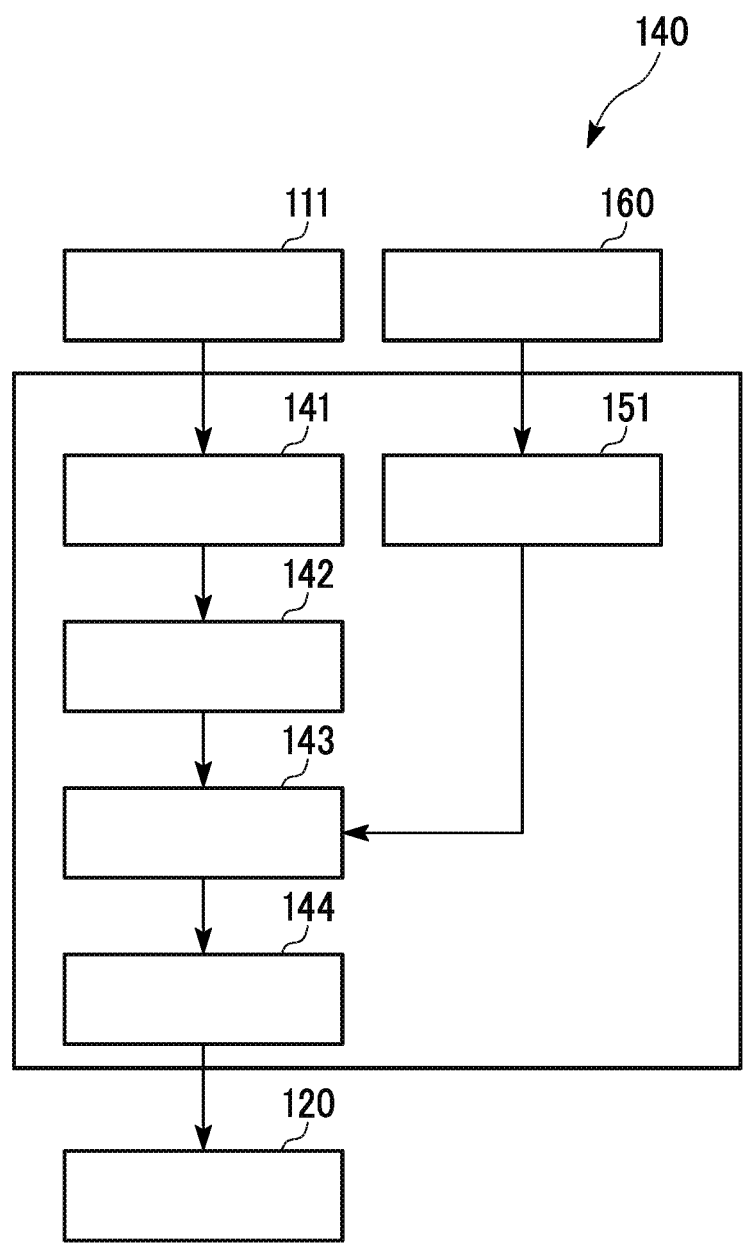
FIG. 2 is a block diagram showing a schematic configuration of a control unit of the artificial heart and lung apparatus of the first embodiment of the present invention.
Figure 3:
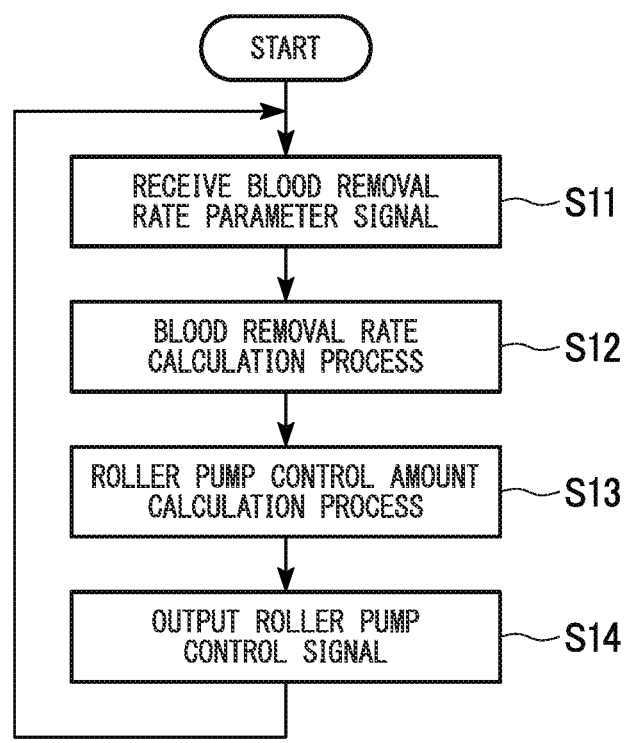
FIG. 3 is a flowchart showing an operational sequence of the control unit in a case where a correction process is not performed in the artificial heart and lung apparatus of the first embodiment of the present invention.

Hereinafter, an artificial heart and lung apparatus (blood circulation system) of a first embodiment of the present invention will be described with reference to FIGS. 1 to 3.

Figure 1:
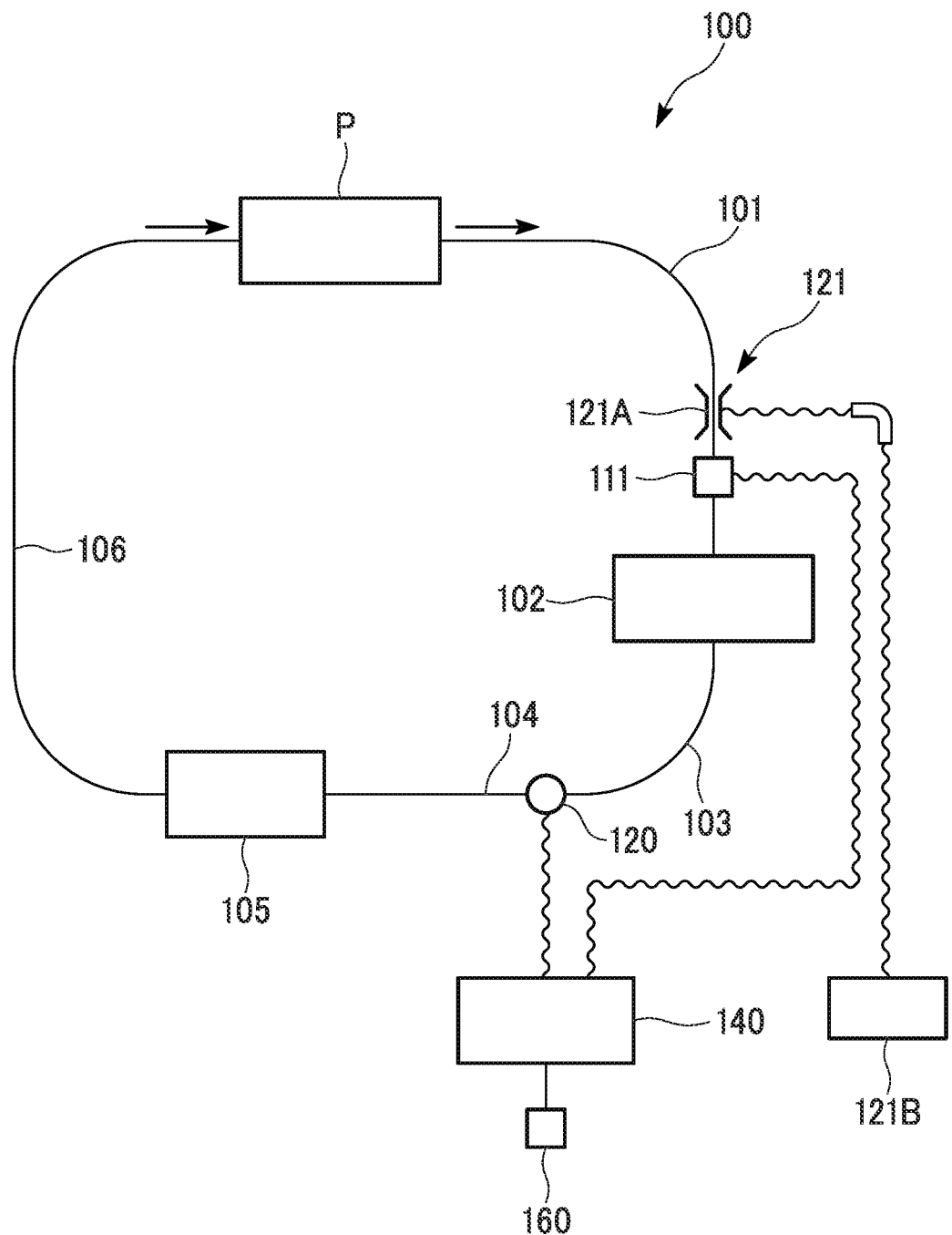
FIG. 1 is a circuit diagram showing a schematic configuration of an artificial heart and lung apparatus of a first embodiment of the present invention.

FIG. 1 is a circuit diagram showing a schematic configuration of the artificial heart and lung apparatus of the first embodiment of the present invention. Reference sign 100 represents an artificial heart and lung apparatus, reference sign 111 represents a blood removal rate sensor, reference sign 120 represents a roller pump, reference sign 140 represents a control unit, and reference sign 160 represents a correction process setting unit.

As shown in FIG. 1, the artificial heart and lung apparatus 100 includes a blood removal line 101; a reservoir 102; a blood line 103; a first blood transfer line (blood transfer line) 104; an artificial lung 105; a second blood transfer line (blood transfer line) 106; a blood removal rate sensor (blood removal rate measurement means) 111; a roller pump (blood transfer pump) 120; a blood removal regulator (flow rate adjustment means) 121; a control unit 140; and a correction process setting unit 160.

The blood removal line 101, the reservoir 102, the blood line 103, the roller pump 120, the first blood transfer line 104, the artificial lung 105, and the second blood transfer line 106 are connected together in the listed sequence. The blood removal regulator 121 and the blood removal rate sensor 111 are disposed in the blood removal line 101 in the listed sequence.

Blood to be removed via the blood removal line 101 is circulated to a patient (human body) P via the first blood transfer line 104 and the second blood transfer line 106.

The blood removal line 101 is a tube formed of resin such as polyvinyl chloride. One end of the blood removal line 101 can be connected to the patient P, and transfers blood, which has been received from a vein, to the reservoir 102.

A sensor or the like (not shown) is provided in the blood removal line 101 so as to monitor the concentration of blood or the concentration of oxygen as necessary. The sensor or the like may be provided in the blood line 103 or the first blood transfer line 104 instead of the blood removal line 101.

The reservoir 102 includes a tank therein, and temporarily stores the transferred blood.

A suction line (not shown) is connected to the reservoir 102 so as to suction blood in a surgical site of the patient P, and a vent line (not shown) is connected to the reservoir 102 so as to suction blood in a right cardiac chamber.

The blood line 103 has the same configuration as that of the blood removal line 101. The upstream side of the blood line 103 is connected to the reservoir 102, and the downstream side of the blood line 103 is connected to the roller pump 120. The blood line 103 transfers the blood, which has been received from the reservoir 102, to the roller pump 120.

The roller pump 120 includes a rotating roller and a tube that is disposed on the outside of the rotating roller and is formed of flexible resin. If the rotating roller rotates and wipes the tube, and blood is suctioned and transferred out, the blood stored in the reservoir 102 is suctioned via the blood line 103, and is transferred to the artificial lung 105 via the first blood transfer line 104.

The rotational speed of the rotating roller is controlled by a rotation control signal output from the control unit 140, and the roller pump 120 suctions and transfers the amount of blood corresponding to the rotational speed of the rotating roller.

The first blood transfer line 104 has the same configuration as that of the blood removal line 101. The upstream side of the first blood transfer line 104 is connected to the roller pump 120, and the downstream side of the first blood transfer line 104 is connected to the artificial lung 105. The first blood transfer line 104 transfers the blood, which has been transferred out from the roller pump 120, to the artificial lung 105.

The artificial lung 105 includes a hollow fiber membrane, a flat membrane, or the like having good gas permeability, and discharges carbon dioxide from and adds oxygen to blood.

A heat exchanger is formed integrally with the artificial lung 105 so as to adjust the temperature of blood.

The second blood transfer line 106 has the same configuration as that of the blood removal line 101, and receives the blood, from which carbon dioxide has been discharged and to which oxygen has been added, from the artificial lung 105, and transfers the blood to an artery of the patient P.

A filter (not shown) is provided in the second blood transfer line 106 so as to remove foreign matter such as thrombi and bubbles from blood.

The blood removal regulator 121 is provided in the blood removal line 101. The blood removal regulator 121 includes a clamper 121A formed of a pair of clamp members; a servo motor (not shown) that operates the clamper 121A; and a blood removal regulator operation unit 121B. An operator changes the cross-sectional area of the blood removal line 101 by adjusting the amount of clamp (the amount of pinch) of the clamper 121A via the servo motor driven by manually operating the blood removal regulator operation unit 121B, and as a result, the removal rate of blood flowing through the blood removal line 101 is adjusted.

The blood removal rate sensor (blood removal rate measurement means) 111 is provided in the blood removal line 101. The blood removal rate sensor 111 transmits a blood removal rate parameter signal, which is measured using an ultrasonic sensor that measures the flow speed of blood via ultrasonic waves, to the control unit 140.

Hereinafter, a schematic configuration of the control unit 140 will be described with reference to FIG. 2. FIG. 2 is a block diagram showing the schematic configuration of the control unit 140 of the first embodiment.

The control unit 140 includes a blood removal rate parameter signal receiving unit 141; a blood removal rate calculation unit 142; a roller pump control amount calculation unit 143; a roller pump control unit 144; and a correction process data receiving unit 151.

The control unit 140 is connected to the blood removal rate sensor 111, and the correction process setting unit 160, and the roller pump 120 via cables.

The correction process setting unit 160 is capable of setting correction process data for correcting measurement errors of the blood removal rate sensor 111, variations of a blood transfer rate characteristic (relationship between the rotational speed and the blood transfer rate) of the roller pump 120 or a deviation of the blood transfer rate with respect to the rotational speed of the roller pump 120 which occurs due to the combination of the blood removal rate sensor 111 and the roller pump 120, or correcting a temporary increase of the blood transfer rate with respect to the blood removal rate.

The correction process data is preferably defined by the amount of deviation (the amount of offset, a ratio, or the like) of the blood transfer rate with respect to the blood removal rate. Alternatively, the correction process data may be defined by other techniques if the correction process data is capable of setting the blood transfer rate of the roller pump 120 to be in a specific range with respect to the blood removal rate.

In the embodiment, the correction process setting unit 160 outputs a correction process execution instruction indicating the execution of a correction process.

In the embodiment, the correction process data is preferably set according to at least one of the measurement errors of the blood removal rate sensor 111, and the amount of a deviation between the blood transfer rate characteristic (relationship between the rotational speed and the blood transfer rate) of the roller pump 120 and a basic blood transfer rate characteristic of the roller pump 120, all of which are confirmed in advance.

The correction process data may be set according to an increase or decrease in the level of blood in the reservoir 102 which occurs after blood circulation starts.

The blood removal rate parameter signal receiving unit 141 is connected to the blood removal rate sensor 111, and receives a blood removal rate parameter signal sent from the blood removal rate sensor 111.

The blood removal rate calculation unit 142 calculates the amount of removed blood according to a signal sent from the blood removal rate parameter signal receiving unit 141. Specifically, it is possible to calculate a blood removal rate by multiplying a blood removal speed (flow rate parameter), which is calculated from the blood removal rate parameter signal, by a flow path area of the blood removal line 101.

The correction process data receiving unit 151 receives the correction process data and the correction process execution instruction, which have been set by the correction process setting unit 160, from the correction process setting unit 160.

The roller pump control amount calculation unit 143 calculates a rotational speed (according to a basic blood transfer rate characteristic), which is required to synchronize the blood transfer rate of the roller pump 120 with the blood removal rate, according to the blood removal rate received from the blood removal rate calculation unit 142. It is possible to calculate the rotational speed according to the basic blood transfer rate characteristic via a data table representing the relationship between the rotational speed of the roller pump 120 and the blood transfer rate, or a calculation expression representing the relationship between the rotational speed of the roller pump 120 and the blood transfer rate.

The rotational speed to be output to the roller pump 120 is calculated according to the rotational speed according to the basic blood transfer rate characteristic and the correction process data received from the correction process data receiving unit 151.

The synchronization of the blood transfer rate of the roller pump 120 with the blood removal rate is one aspect in which the blood transfer rate is controlled to be in a specific range (for example, in a range represented by a ratio to the blood removal rate, or in a range represented by a difference in flow rate with respect to the blood removal rate) with respect to the blood removal rate.

The roller pump control unit 144 outputs a signal, which corresponds to a control amount (corrected rotational speed) received from the roller pump control amount calculation unit 143, to the roller pump 120.

Hereinafter, an operational sequence in a case where the control unit 140 of the artificial heart and lung apparatus 100 of the first embodiment does not perform a correction process will be described with reference to FIG. 3. FIG. 3 is a flowchart showing the operational sequence of the control unit 140 in a case where a correction process is not performed in the artificial heart and lung apparatus 100.

(1) First, the control unit 140 receives a blood removal rate parameter signal (S11).

(2) Subsequently, the control unit 140 calculates a blood removal rate according to the received blood removal rate parameter signal (S12).

(3) Subsequently, the control unit 140 calculates a control amount (rotational speed) according to a basic blood transfer rate characteristic of the roller pump 120 according to the received blood removal rate (S13).

(4) Subsequently, the control unit 140 outputs a signal, which corresponds to the control amount, to the roller pump 120 (S14).

If S14 is executed, the process proceeds to S11.

S11 to S14 are repeatedly executed at predetermined intervals until a surgery is complete and blood circulation ends.

Figure 4:
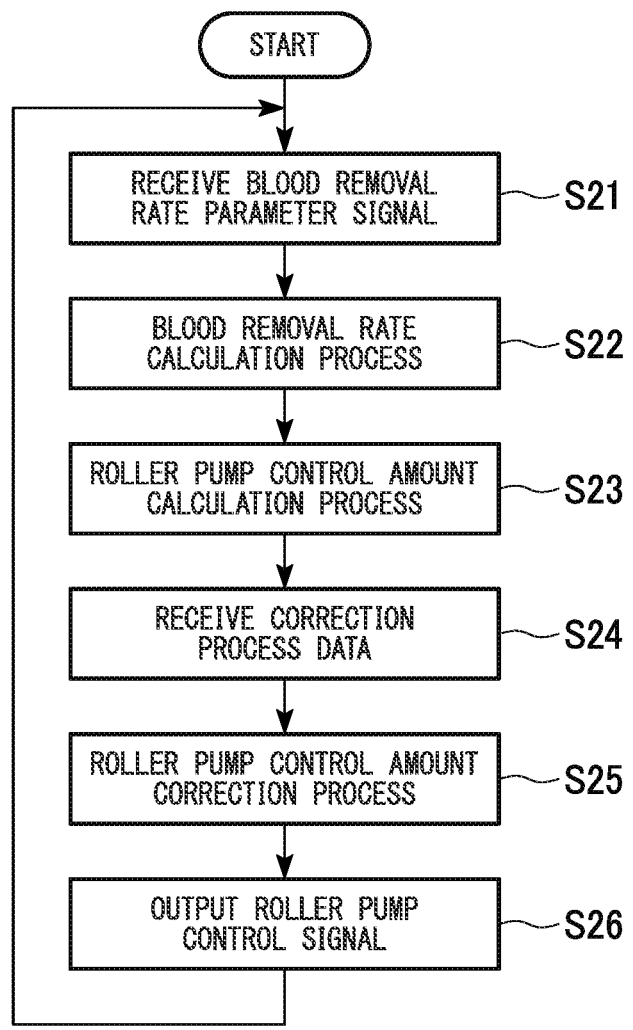
FIG. 4 is a flowchart showing an operational sequence of the control unit in a case where a correction process is performed in the artificial heart and lung apparatus of the first embodiment of the present invention.

Hereinafter, an operational sequence in a case where the control unit 140 of the artificial heart and lung apparatus 100 of the first embodiment performs a correction process will be described with reference to FIG. 4. FIG. 4 is a flowchart showing the operational sequence of the control unit 140 in a case where a correction process is performed in the artificial heart and lung apparatus 100.

(1) First, the control unit 140 receives a blood removal rate parameter signal (S21).

(2) Subsequently, the control unit 140 calculates a blood removal rate according to the received blood removal rate parameter signal (S22).

(3) Subsequently, the control unit 140 calculates a rotational speed according to on the basic blood transfer rate characteristic of the roller pump 120 according to the received blood removal rate (S23).

(4) Subsequently, the control unit 140 receives correction process data (S24).

(5) Subsequently, the control unit 140 corrects the rotational speed, which has been calculated in S23 according to the basic blood transfer rate characteristic of the roller pump 120, according to the correction process data, and calculates a control amount (corrected rotational speed) to be output to the roller pump 120 (S25).

(6) Subsequently, the control unit 140 outputs a signal, which corresponds to the control amount (corrected rotational speed), to the roller pump 120 (S26).

If S26 is executed, the process proceeds to S21.

S21 to S26 are repeatedly executed at predetermined intervals until a surgery is complete and blood circulation ends.

In the artificial heart and lung apparatus 100 of the first embodiment, the control unit 140 controls the roller pump 120 such that the blood transfer rate of the roller pump 120 is synchronized with the flow rate of removed blood flowing through the blood removal line 101. Accordingly, the amount of blood corresponding to the amount of removed blood can be transferred to the patient P via the first blood transfer line 104, the artificial lung 105, and the second blood transfer line 106.

As a result, even if the blood removal rate changes, it is possible to stably circulate blood at a suitable flow rate.

In the artificial heart and lung apparatus 100 of the first embodiment, the correction process setting unit 160 is provided, and the control unit 140 corrects deviations between a measurement characteristic of the blood removal rate sensor 111 and the blood transfer rate characteristic of the roller pump 120 according to correction process data input to the correction process setting unit 160. Accordingly, the artificial heart and lung apparatus 100 of the first embodiment is capable of efficiently synchronizing the blood transfer rate of the roller pump 120 with the blood removal rate.

Since the artificial heart and lung apparatus 100 of the first embodiment includes the roller pump 120 as the blood transfer pump, the artificial heart and lung apparatus 100 is unlikely to be affected by pressure, and is capable of transferring blood at a stable blood transfer rate.

In the artificial heart and lung apparatus 100 of the first embodiment, the blood removal regulator 121 is provided in the blood removal line 101, and thus, the flow rate of blood removed via the blood removal line 101 is suitably adjusted.

The artificial heart and lung apparatus 100 of the first embodiment includes the reservoir 102. The artificial heart and lung apparatus 100 is capable of synchronizing a blood transfer rate with a blood removal rate or adjusting the blood transfer rate to be in a specific range with respect to the blood removal rate, and the occurrence of excessive negative pressure is prevented. Accordingly, an auxiliary circulation apparatus (blood circulation system) in which the reservoir 102 is not provided and the roller pump 120 is adopted may be used as the artificial heart and lung apparatus 100 shown in FIG. 1.

Second Embodiment

Hereinafter, an artificial heart and lung apparatus (blood circulation system) of a second embodiment of the present invention will be described with reference to FIGS. 5 to 8.

Figure 5:
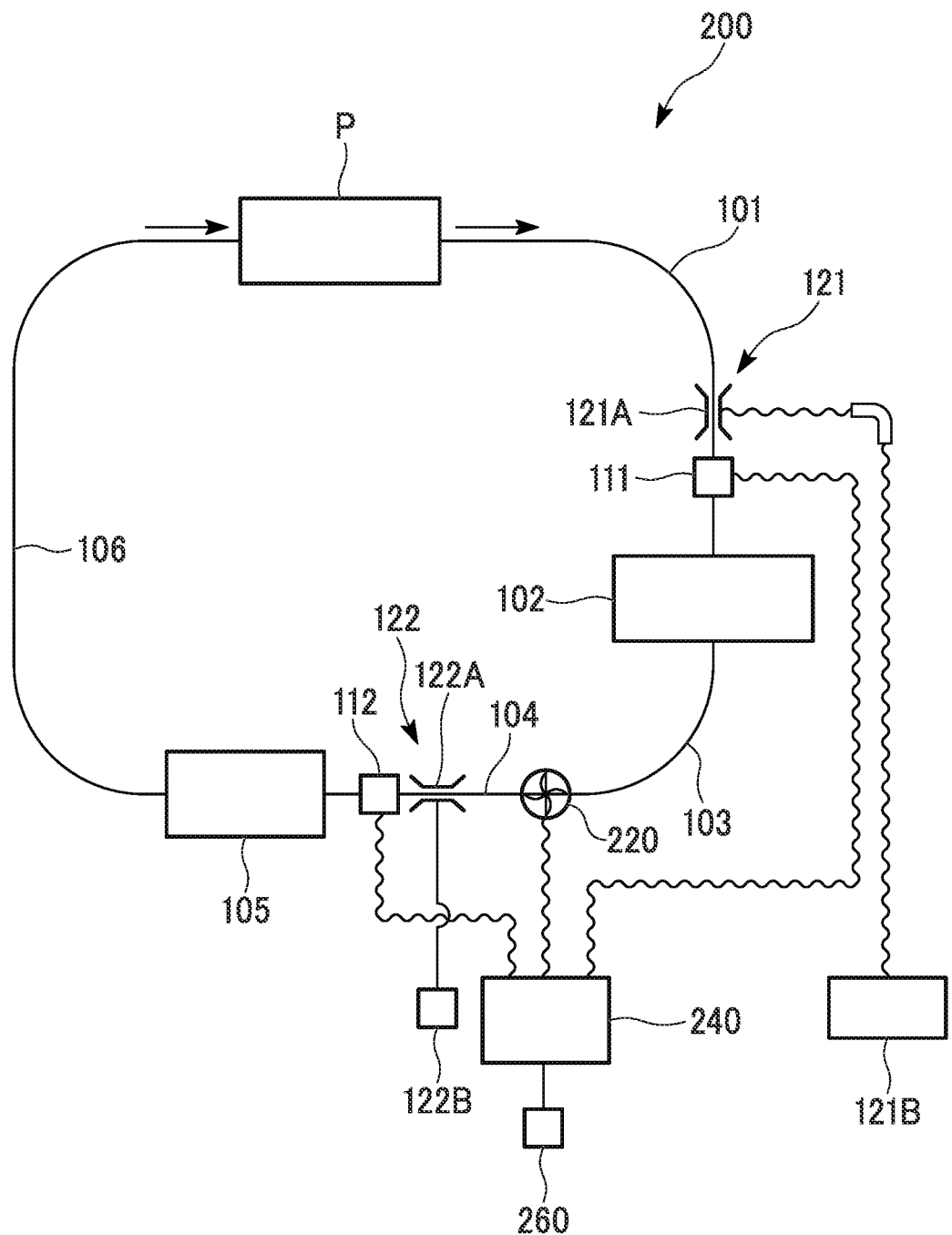
FIG. 5 is a circuit diagram showing a schematic configuration of an artificial heart and lung apparatus of a second embodiment of the present invention.

FIG. 5 is a circuit diagram showing a schematic configuration of the artificial heart and lung apparatus of the second embodiment of the present invention. Reference sign 200 represents an artificial heart and lung apparatus, reference sign 112 represents a blood transfer rate sensor (blood transfer rate measurement means), reference sign 220 represents a centrifugal pump (blood transfer pump), reference sign 260 represents a correction process setting unit, and reference sign 240 represents a control unit.

As shown in FIG. 5, an artificial heart and lung apparatus 200 includes the blood removal line 101; the reservoir 102; the blood line 103; a centrifugal pump 220; the first blood transfer line (blood transfer line) 104; the artificial lung 105; the second blood transfer line (blood transfer line) 106; the blood removal rate sensor 111; a blood transfer rate sensor 112; the blood removal regulator (flow rate adjustment means) 121; a blood transfer regulator 122; a control unit 240; and a correction process setting unit 260.

The blood removal line 101, the reservoir 102, the blood line 103, the centrifugal pump 220, the first blood transfer line 104, the artificial lung 105, and the second blood transfer line 106 are connected together in the listed sequence. The blood removal regulator 121 and the blood removal rate sensor 111 are disposed in the blood removal line 101 in the listed sequence. The blood transfer regulator 122 and the blood transfer rate sensor 112 are disposed in the first blood transfer line 104 in the listed sequence.

The blood removal line 101, the reservoir 102, the blood line 103, the first blood transfer line 104, the artificial lung 105, the second blood transfer line 106, the blood removal rate sensor 111, and the blood removal regulator 121 are the same as those of the first embodiment, and thus, a description thereof will be omitted.

Similar to the blood removal rate sensor 111, an ultrasonic sensor is used as the blood transfer rate sensor (blood transfer rate measurement means) 112. The blood transfer rate sensor 112 sends a measurement result to the control unit 240.

The centrifugal pump 220 suctions blood stored in the reservoir 102 via the blood line 103, and transfers the blood to the artificial lung 105 via the first blood transfer line 104 by rotating impeller blades via an AC servo motor or a DC servo motor.

The rotational speed of the centrifugal pump 220 is feedback controlled such that a blood transfer rate measured by the blood transfer rate sensor 112 is synchronized with a blood removal rate measured by the blood removal rate sensor 111.

The blood transfer regulator 122 is provided in the first blood transfer line 104. The blood transfer regulator 122 includes a clamper 122A formed of a pair of clamp members; a servo motor (not shown) that operates the clamper 122A; and a blood transfer regulator operation unit 122B. An operator blocks the first blood transfer line 104 by adjusting the amount of clamp (the amount of pinch) of the clamper 122A via the servo motor driven by manually operating the blood transfer regulator operation unit 122B, and thus, the back flowing of blood when the centrifugal pump 220 stops is prevented.

Figure 6:
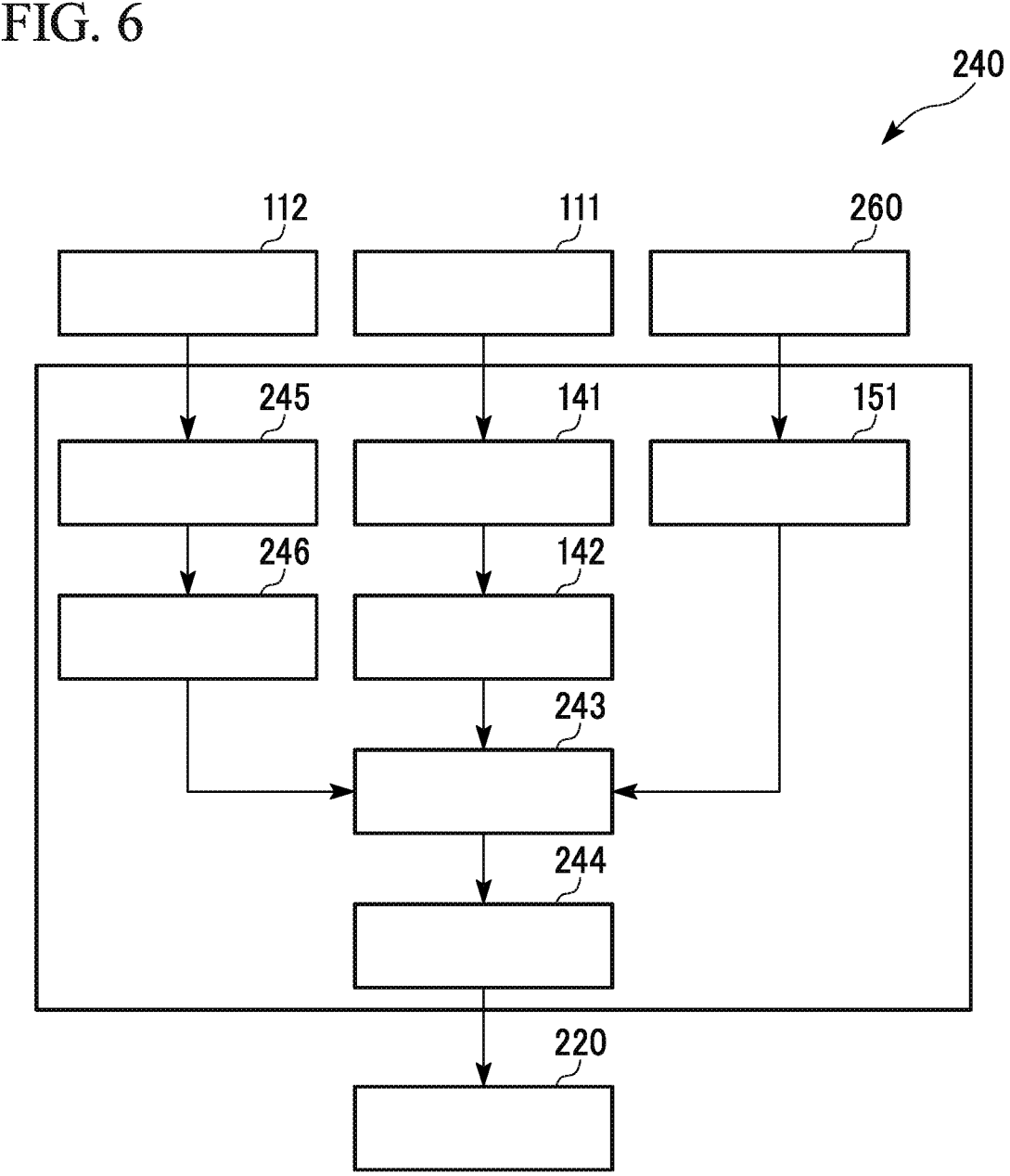
FIG. 6 is a block diagram showing a schematic configuration of a control unit of the artificial heart and lung apparatus of the second embodiment of the present invention.

Hereinafter, a schematic configuration of the control unit 240 will be described with reference to FIG. 6. FIG. 6 is a block diagram showing the schematic configuration of the control unit 240 of the second embodiment.

The control unit 240 includes the blood removal rate parameter signal receiving unit 141; the blood removal rate calculation unit 142; a centrifugal pump control amount calculation unit 243; a centrifugal pump control unit 244; a blood transfer rate parameter signal receiving unit 245; a blood transfer rate calculation unit 246; and the correction process data receiving unit 151.

The control unit 240 is connected to the blood removal rate sensor 111, the blood transfer rate sensor 112, the correction process setting unit 260, and the centrifugal pump 220 via cables.

The blood removal rate parameter signal receiving unit 141, the blood removal rate calculation unit 142, and the correction process data receiving unit 151 are the same as those of the first embodiment, and thus, a description thereof will be omitted.

Since the centrifugal pump 220 of the second embodiment is feedback controlled, there is a low need to take into consideration blood transfer rate errors which are caused by a blood transfer rate characteristic. In contrast, the blood removal rate sensor 111 and the blood transfer rate sensor 112 have different measurement characteristics. If the measurement characteristics (measurement errors) of the blood removal rate sensor 111 and the blood transfer rate sensor 112 are different from each other, a deviation between a blood transfer rate and a blood removal rate may occur due to the combination of the blood removal rate sensor 111 and the blood transfer rate sensor 112. The deviation between the blood transfer rate and the blood removal rate occurring due to the combination of the blood removal rate sensor 111 and the blood transfer rate sensor 112 is preferably corrected.

The correction process setting unit 260 sets correction process data for correcting a deviation occurring due to the combination of the blood removal rate sensor 111 and the blood transfer rate sensor 112, or correcting a temporary increase of the blood transfer rate with respect to the blood removal rate.

The correction process data is preferably defined by the amount of deviation (the amount of offset, a ratio, or the like) of the blood transfer rate with respect to the blood removal rate. Alternatively, the correction process data may be defined by other techniques if the correction process data is capable of setting the blood transfer rate of the centrifugal pump 220 to be in a specific range with respect to the blood removal rate. In the embodiment, the correction process setting unit 260 outputs a correction process execution instruction indicating the execution of a correction process.

In the embodiment, the correction process data is preferably set according to the amount of a deviation between the measurement characteristic of the blood removal rate sensor 111 and the measurement characteristic of the blood transfer rate sensor 112 which have been confirmed in advance.

The correction process data may be set according to an increase or decrease in the level of blood in the reservoir 102 which occurs after blood circulation starts.

The blood transfer rate parameter signal receiving unit 245 is connected to the blood transfer rate sensor 112, and receives a blood transfer rate parameter signal sent from the blood transfer rate sensor 112.

The blood transfer rate calculation unit 246 calculates a blood transfer rate according to a signal sent from the blood transfer rate parameter signal receiving unit 245. Specifically, it is possible to calculate a blood removal rate by multiplying a blood transfer speed (flow rate parameter), which is calculated from the blood transfer rate parameter signal, by a flow path area of the first blood transfer line 104.

First, the centrifugal pump control amount calculation unit 243 calculates a target blood transfer rate, which is required to synchronize the blood transfer rate of the centrifugal pump 220 with the blood removal rate, according to the blood removal rate received from the blood removal rate calculation unit 142. Subsequently, a corrected target blood transfer rate is calculated by correcting the target blood transfer rate according to the correction process data received from the correction process data receiving unit 151. The centrifugal pump control amount calculation unit 243 increases or decreases a control amount (corrected rotational speed) to be output to the centrifugal pump 220 by comparing the corrected target blood transfer rate to the blood transfer rate received from the blood transfer rate calculation unit 246.

The synchronization of the blood transfer rate of the centrifugal pump 220 with the blood removal rate is one aspect in which the blood transfer rate is controlled to be in a specific range (for example, in a range represented by a ratio to the blood removal rate, or in a range represented by a difference in flow rate with respect to the blood removal rate) with respect to the blood removal rate.

In a case where the correction process is not performed, and there is no deviation between the measurement characteristics, the centrifugal pump 220 may be controlled via a rotational speed.

The correction process data receiving unit 151 receives the correction process data and the correction process execution instruction, which have been set by the correction process setting unit 260, from the correction process setting unit 260.

The centrifugal pump control unit 244 outputs a signal, which corresponds to the rotational speed, to the centrifugal pump 220 according to the control amount (corrected rotational speed) received from the centrifugal pump control amount calculation unit 243.

Figure 7:
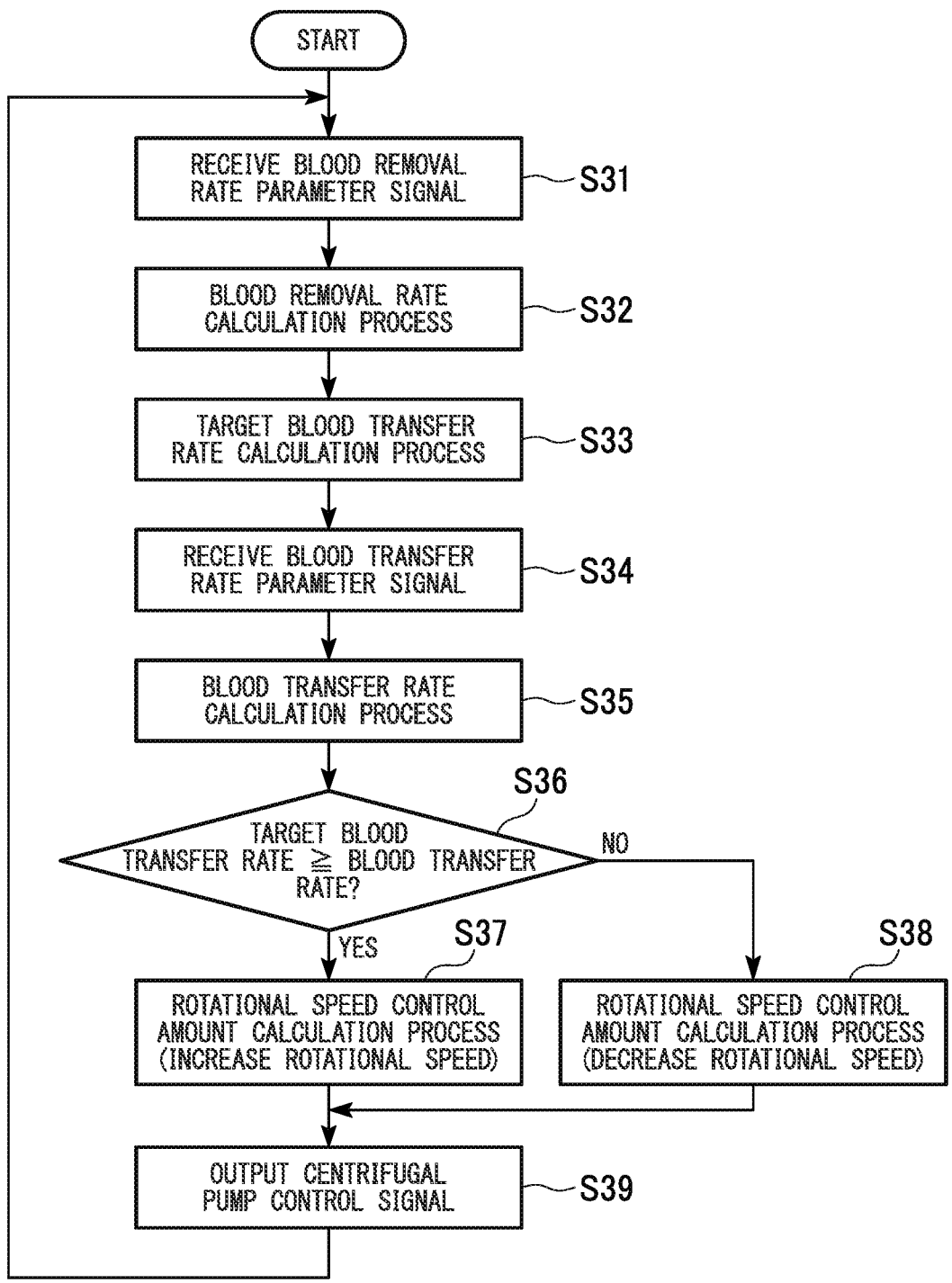
FIG. 7 is a flowchart showing an operational sequence of the control unit in a case where a correction process is not performed in the artificial heart and lung apparatus of the second embodiment of the present invention.

Hereinafter, an operational sequence in a case where the control unit 240 of the artificial heart and lung apparatus 200 of the second embodiment does not perform a correction process will be described with reference to FIG. 7. FIG. 7 is a flowchart showing the operational sequence of the control unit 240 in a case where a correction process is not performed in the artificial heart and lung apparatus 200.

(1) First, the control unit 240 receives a blood removal rate parameter signal (S31).

(2) Subsequently, the control unit 240 calculates a blood removal rate according to the received blood removal rate parameter signal (S32).

(3) Subsequently, the control unit 240 calculates a target blood transfer rate according to the blood removal rate calculated in S32 (S33).

(4) Subsequently, the control unit 240 receives a blood transfer rate parameter signal (S34).

(5) Subsequently, the control unit 240 calculates a blood transfer rate according to the received blood transfer rate parameter signal (S35).

(6) Subsequently, the control unit 240 compares the target blood transfer rate calculated in S33 to the blood transfer rate calculated in S35, calculates (the target blood transfer rate—the blood transfer rate), and determines whether the target blood transfer rate is greater than or equal to the blood transfer rate (S36).

If the target blood transfer rate is greater than or equal to the blood transfer rate (S36: Yes), the process proceeds to S37. If the target blood transfer rate is less than the blood transfer rate (S36: No), the process proceeds to S38.

(7) The control unit 240 calculates a control amount (increased rotational speed) for the centrifugal pump 220 according to a difference (=(the target blood transfer rate—the blood transfer rate)) calculated in S36 (S37).

If the target blood transfer rate is equal to the blood transfer rate, the control amount (increased rotational speed) becomes zero.

(8) The control unit 240 calculates a control amount (decreased rotational speed) for the centrifugal pump 220 according to a difference (=(the target blood transfer rate—the blood transfer rate)) calculated in S36 (S38).

(9) Subsequently, the control unit 240 outputs a signal, which corresponds to the control amount calculated in S37 or S38, to the centrifugal pump 220 (S39).

If S39 is executed, the process proceeds to S31.

S31 to S39 are repeatedly executed at predetermined intervals until a surgery is complete and blood circulation ends.

Figure 8:
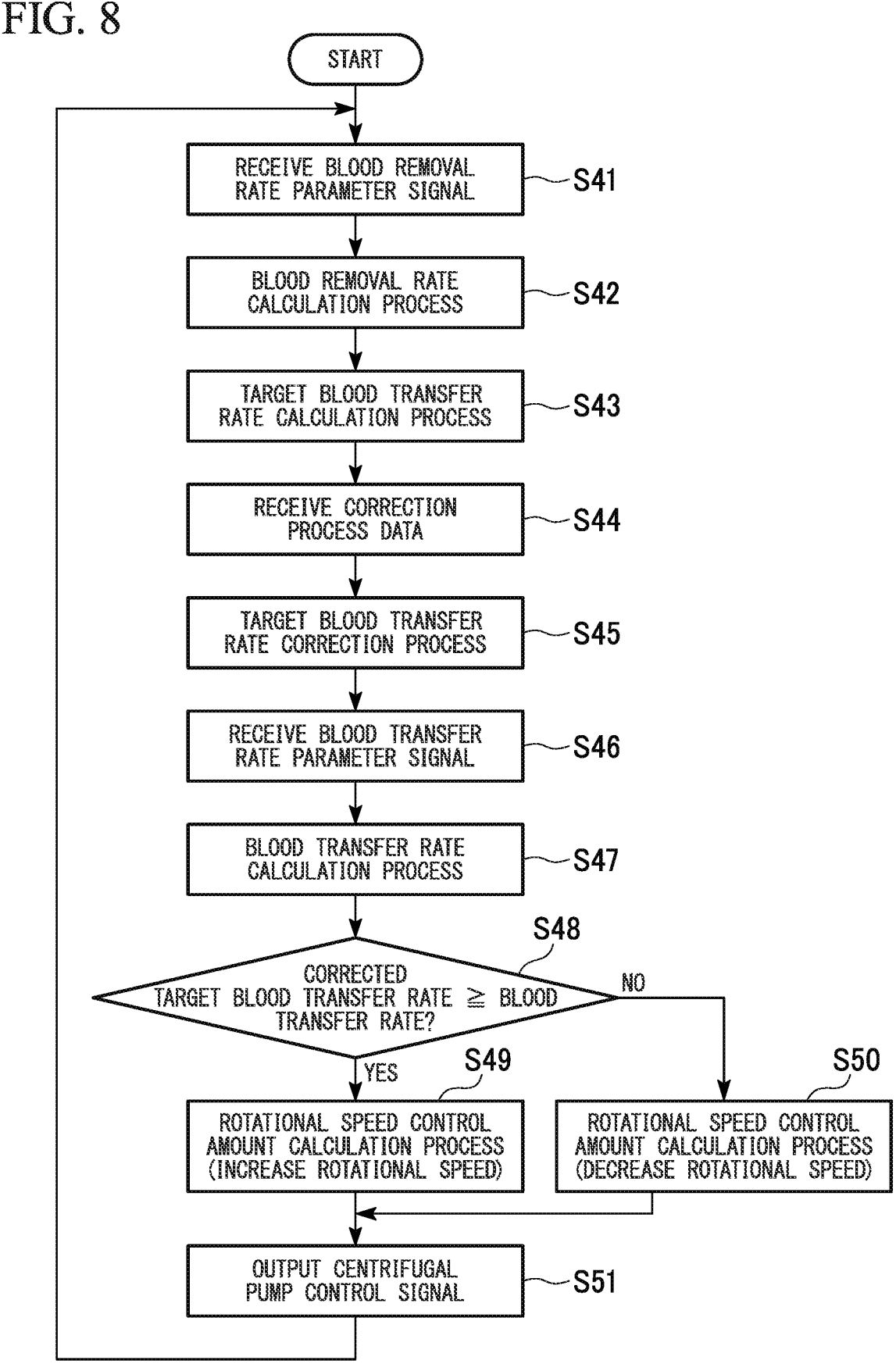
FIG. 8 is a flowchart showing an operational sequence of the control unit in a case where a correction process is performed in the artificial heart and lung apparatus of the second embodiment of the present invention.
Figure 9:
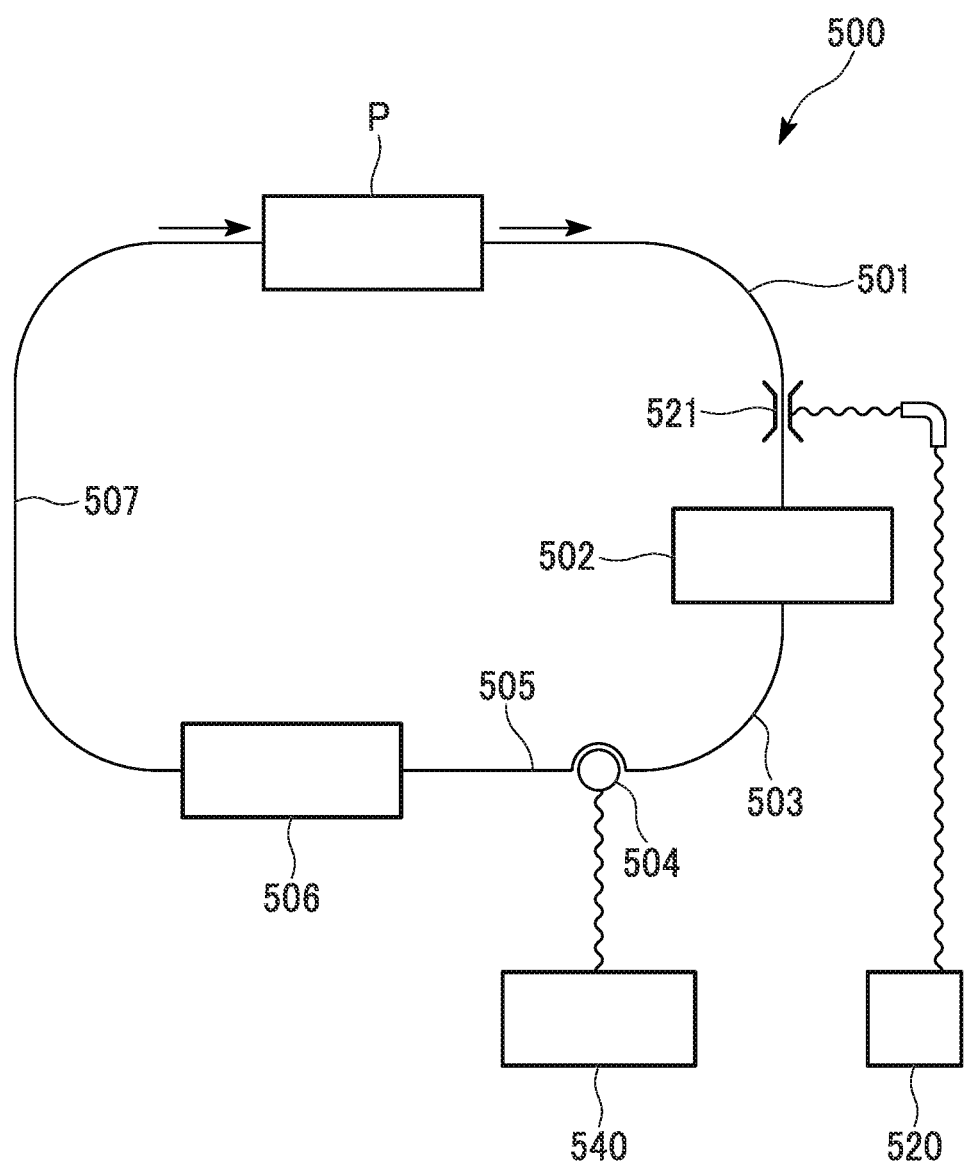
FIG. 9 is a circuit diagram showing a schematic configuration of an artificial heart and lung apparatus in the related art.

Hereinafter, an operational sequence in a case where the control unit 240 of the artificial heart and lung apparatus 200 of the second embodiment performs a correction process will be described with reference to FIG. 8. FIG. 8 is a flowchart showing the operational sequence of the control unit 240 in a case where a correction process is performed in the artificial heart and lung apparatus 200.

(1) First, the control unit 240 receives a blood removal rate parameter signal (S41).

(2) Subsequently, the control unit 240 calculates a blood removal rate according to the received blood removal rate parameter signal (S42).

(3) Subsequently, the control unit 240 calculates a target blood transfer rate according to the blood removal rate calculated in S42 (S43).

(4) Subsequently, the control unit 240 receives correction process data (S44).

(5) Subsequently, the control unit 240 calculates a corrected target blood transfer rate by correcting the target blood transfer rate according to the correction process data (S45).

(6) Subsequently, the control unit 240 receives a blood transfer rate parameter signal (S46).

(7) Subsequently, the control unit 240 calculates a blood transfer rate according to the received blood transfer rate parameter signal (S47).

(8) Subsequently, the control unit 240 compares the corrected target blood transfer rate corrected in S45 to the blood transfer rate calculated in S47, calculates (the corrected target blood transfer rate—the blood transfer rate), and determines whether the corrected target blood transfer rate is greater than or equal to the blood transfer rate (S48).

If the corrected target blood transfer rate is greater than or equal to the blood transfer rate (S48: Yes), the process proceeds to S49. If the corrected target blood transfer rate is less than the blood transfer rate (S48: No), the process proceeds to S50.

(9) The control unit 240 calculates a control amount (increased rotational speed) for the centrifugal pump 220 according to a difference (=(the corrected target blood transfer rate—the blood transfer rate)) calculated in S48 (S49).

If the corrected target blood transfer rate is equal to the blood transfer rate, the control amount (increased rotational speed) becomes zero.

(10) The control unit 240 calculates a control amount (decreased rotational speed) for the centrifugal pump 220 according to a difference (=(the corrected target blood transfer rate—the blood transfer rate)) calculated in S48 (S50).

(11) Subsequently, the control unit 240 outputs a signal, which corresponds to the control amount calculated in S49 or S50, to the centrifugal pump 220 (S51).

If S51 is executed, the process proceeds to S41.

S41 to S51 are repeatedly executed at predetermined intervals until a surgery is complete and blood circulation ends.

Since the control unit 240 performs adjustment such that the flow rate of blood to be transferred to the first blood transfer line 104 is synchronized with the flow rate of removed blood flowing through the blood removal line 101, the artificial heart and lung apparatus 200 of the second embodiment is capable of transferring the same amount of blood as the amount of removed blood to the patient P.

As a result, even if the blood removal rate changes, it is possible to ensure a suitable blood transfer rate corresponding to the blood removal rate, and to perform suitable blood circulation.

In the artificial heart and lung apparatus 200 of the second embodiment, the correction process setting unit 260 is provided, and the control unit 240 corrects a deviation between the measurement characteristics of the blood removal rate sensor 111 and the blood transfer rate sensor 112 according to correction process data input to the correction process setting unit 260. As a result, it is possible to efficiently synchronize the blood transfer rate of the centrifugal pump 220 with the blood removal rate.

In the artificial heart and lung apparatus 200 of the second embodiment, the centrifugal pump 220 is used as a blood transfer pump, and thus, it is possible to promptly transfer blood at a stable blood transfer rate.

In the artificial heart and lung apparatus 200 of the second embodiment, the blood removal regulator 121 is provided in the blood removal line 101, and thus, the blood removal rate is suitably adjusted.

The blood transfer regulator 122 is provided in the first blood transfer line 104, and is capable of preventing the back flowing of blood by blocking the first blood transfer line 104 when the centrifugal pump 220 stops.

The present invention is not limited to the embodiments, and changes can be made to the embodiments in various forms insofar as the changes do not depart from the concept of the invention.

In the artificial heart and lung apparatuses 100 and 200 of the embodiments, the blood transfer rate is synchronized with the blood removal rate. Alternatively, the blood transfer rate may be adjusted to be in a specific range with respect to the blood removal rate.

In the embodiments, the artificial heart and lung apparatuses 100 and 200 respectively include the correction process setting units 160 and 260. Alternatively, setting as to whether the correction process setting units 160 and 260 are included may be arbitrarily performed.

In a case where the correction process setting units 160 and 260 are included, the correction process setting units 160 and 260 may be externally attachably included.

In the embodiments, the blood removal rate sensor 111 and the blood transfer rate sensor 112 which measure the flow speed of blood are respectively used as blood removal rate measurement means and blood transfer rate measurement means. Alternatively, a blood removal rate and a blood transfer rate may be measured by measuring a blood removal rate parameter (including a blood removal rate) other than a blood removal speed and a blood transfer rate parameter (including a blood transfer rate) other than a blood transfer speed.

In the embodiments, ultrasonic sensors are used as the blood removal rate sensor 111 and the blood transfer rate sensor 112. Alternatively, various well-known flow rate measurement means using laser, infrared light, or the like may be used instead of an ultrasonic sensor.

In the embodiments, the roller pump 120 and the centrifugal pump 220 are used as blood transfer pumps. Alternatively, other types of blood transfer pumps may be used.

In the first embodiment, flow rate adjustment means is not provided in the blood transfer line. Alternatively, flow rate sensors (flow rate parameter measurement means) such as ultrasonic sensors may be suitably provided in the first blood transfer line 104 and the second blood transfer line 106.

In the first embodiment, the blood removal regulator 121 is provided as flow rate adjustment means, and in the second embodiment, the blood removal regulator 121 and the blood transfer regulator 122 are provided as flow rate adjustment means. Alternatively, in the first and second embodiments, neither the blood removal regulator 121 nor the blood transfer regulator 122 may be provided. In a case where flow rate adjustment means is provided, setting as to whether either or both of the blood removal regulator 121 and the blood transfer regulator 122 are provided may be suitably performed, and portions of a blood removal line and a blood transfer line, in which the blood removal regulator 121 and the blood transfer regulator 122 are provided, may be suitably set.

Flow rate measurement means other than the blood removal regulator 121 and the blood transfer regulator 122 may be provided.

In the first and second embodiments, the blood removal regulator 121 and the blood removal rate sensor 111 are disposed in the blood removal line 101 in the listed sequence. Alternatively, the blood removal rate sensor 111 and the blood removal regulator 121 are disposed in the listed sequence.

In the second embodiment, the blood transfer regulator 122 and the blood transfer rate sensor 112 are disposed in the first blood transfer line 104 in the listed sequence. Alternatively, the blood transfer regulator 122 and the blood transfer rate sensor 112 may be disposed in the second blood transfer line 106 instead of the first blood transfer line 104. The blood transfer rate sensor 112 and the blood transfer regulator 122 may be disposed in the listed sequence.

In the embodiments, FIGS. 3, 4, 7, and 8 show examples of the flowcharts showing schematic steps of controlling the roller pump 120 and the centrifugal pump 220 of the present invention. Alternatively, control may be performed via methods (algorithms) other than the methods shown in the flowcharts.

In the embodiments, a blood circulation system is applied to the artificial heart and lung apparatuses 100 and 200. Alternatively, the present invention may be applied to an auxiliary circulation apparatus (blood circulation system) and the like, which does not include a reservoir and is used in a cardiac surgery operation, other than an artificial heart and lung apparatus.

INDUSTRIAL APPLICABILITY

In a case where a blood circulation system of the present invention circulates removed blood via a blood transfer pump, the blood circulation system is capable of stably transferring blood at a suitable flow rate.

REFERENCE SIGNS LIST

P: PATIENT (HUMAN BODY)
100, 200: ARTIFICIAL HEART AND LUNG APPARATUS (BLOOD CIRCULATION SYSTEM)
101: BLOOD REMOVAL LINE
102: RESERVOIR
104: FIRST BLOOD TRANSFER LINE (BLOOD TRANSFER LINE)
105: ARTIFICIAL LUNG
106: SECOND BLOOD TRANSFER LINE (BLOOD TRANSFER LINE)
111: BLOOD REMOVAL RATE SENSOR (BLOOD REMOVAL RATE MEASUREMENT MEANS)
112: BLOOD TRANSFER RATE SENSOR (BLOOD TRANSFER RATE MEASUREMENT MEANS)
120: ROLLER PUMP (BLOOD TRANSFER PUMP)
121: BLOOD REMOVAL REGULATOR (FLOW RATE ADJUSTMENT MEANS)
122: BLOOD TRANSFER REGULATOR (FLOW RATE ADJUSTMENT MEANS)
140, 240: CONTROL UNIT
160, 260: CORRECTION PROCESS SETTING UNIT
220: CENTRIFUGAL PUMP (BLOOD TRANSFER PUMP)

What is claimed is:

1. A blood circulation system that can be connected to a human body, the system comprising:
   a roller pump;
   a blood removal line through which blood removed from the human body flows to the roller pump;
   a blood transfer line that transfers blood, which is sent from the roller pump, to the human body;
   a blood removal rate measurement means that is provided in the blood removal line to measure a blood removal rate parameter of blood flowing through the blood removal line; and
   a control unit,
   wherein the control unit is programmed to control a blood transfer rate of the roller pump by controlling a rotational speed of the roller pump with a control signal, such that a transfer rate of blood flowing through the blood transfer line is synchronized with a removal rate calculated from the blood removal rate parameter.

2. The blood circulation system according to claim 1, further comprising:
   a correction process setting unit,
   wherein according to correction process data input to the correction process setting unit, the control unit performs correction such that the blood transfer rate of the roller pump corresponds to the blood removal rate.

3. The blood circulation system according to claim 1, wherein flow rate adjustment means is provided in the blood removal line.

4. A blood circulation method using a blood circulation system that can be connected to a human body,
   the blood circulation system comprising:
      a roller pump;
      a blood removal line through which blood removed from the human body flows to the roller pump; and
      a blood transfer line that transfers blood, which is sent from the roller pump, to the human body,
   the blood circulation method comprising:
      measuring a blood removal rate parameter of blood flowing through the blood removal line;
      calculating a removal rate from the blood removal rate parameter; and
      controlling a blood transfer rate of the roller pump by controlling a rotational speed of the roller pump, such that a transfer rate of blood flowing through the blood transfer line is synchronized with the removal rate.

* * * * *